United States Patent [19]
Leavitt et al.

[11] Patent Number: 5,939,538
[45] Date of Patent: Aug. 17, 1999

[54] METHODS AND COMPOSITIONS FOR INHIBITING HIV INFECTION OF CELLS BY CLEAVING HIV CO-RECEPTOR RNA

[75] Inventors: Markley C. Leavitt, La Jolla; Richard Tritz, San Diego; Yu Feng, San Diego; Jack Barber, San Diego; Mang Yu, San Diego, all of Calif.

[73] Assignee: Immusol Incorporated, San Diego, Calif.

[21] Appl. No.: 08/770,235

[22] Filed: Dec. 19, 1996

Related U.S. Application Data

[60] Provisional application No. 60/027,875, Oct. 25, 1996.

[51] Int. Cl.$^6$ .................................................. C07H 21/02
[52] U.S. Cl. .................................. 536/23.1; 935/3; 935/5
[58] Field of Search ................................ 536/23.1, 23.2; 435/320.1, 172.1, 974; 424/184.1, 278.1

[56] References Cited

U.S. PATENT DOCUMENTS 5,254,678  10/1993  Haseloff et al. ........................ 536/23.2

OTHER PUBLICATIONS

Feng, et al., Science 272:872–877, 1996.
Berson, et al. (1996) J. Virol 70 (9): 6288–95.
Doranz, et al. (1996) Cell 85 (7): 1149–58.
Alkhatib, et al. (1996) Science 272 (5270): 1955–8.
Deng, et al. (1996) Nature 381 (6584): 661–6.
Combadiere, et al. (1996) J. Leukoc. Biol. 60 (1), 147–152.
Castanotto, et al. (1994) Advances in Pharmacology 25: 289–317.
Anderson, et al. (1994) Nucleic Acids Research 22(6): 1096–1100.
Naldini, et al. (1996) Science 262:267.
Akkina, et al. (1996) J Virol 70:2581.
Doranz et al., "A Dual–Tropic Primary HIV–1 Isolate That Uses Fusin and the β–Chemokine Receptors CKR–5, CKR–3, and CKR–2b as Fusion Cofactors", Cell, vol. 85, No. 7(Jun. 28, 1996), pp. 1149–1158.
Samson et al. "Resistance to HIV–1 Infection in Caucasian Individuals Bearing Mutant Alleles of the CCR–5 Chemokine Receptor Gene", Nature, vol. 382, No. 6593(Aug. 22, 1996), pp. 722–725. Q1.N2.
John M. Burke, "Clearing the Way for Ribozymes", Nature Biotechnology 15:414–415 (1997).

Primary Examiner—Jeffrey Stucker
Attorney, Agent, or Firm—Townsend and Townsend and Crew LLP

[57] ABSTRACT

Methods of inhibiting HIV infection by blocking HIV co-receptor RNA expression are provided. Ribozymes which cleave HIV co-receptor RNA and inhibit HIV infection of cells are also provided. Co-receptor targets include fusin and CKR5.

13 Claims, 1 Drawing Sheet

METHODS AND COMPOSITIONS FOR INHIBITING HIV INFECTION OF CELLS BY CLEAVING HIV CO-RECEPTOR RNA

This application claims priority to provisional application Ser. No. 60/027,875, filed Oct. 25, 1996, now abandoned.

BACKGROUND OF THE INVENTION

Infection of cells by human immunodeficiency virus (HIV) is mediated by binding to CD4 expressed on the surface of the cell and fusion with the cellular membrane. Fusion does not occur in most nonhuman cells even when they express human CD4, indicating that one or more human accessory factors also mediate virus infection. Recently, a seven-transmembrane domain protein was shown to serve as an accessory factor for T-cell-tropic (T-tropic) HIV-1 isolates. See, Feng et al., Science 272:872–877, 1996, and Berson et al. (1996) J Virol 70 (9): 6288–95. Expression of this glycoprotein, termed fusin, in murine, feline, simian and quail cell lines, in conjunction with human CD4, rendered these cells permissive for HIV-1 envelope glycoprotein (Env)-mediated infection. Expression of CD4 or fusin alone did not permit infection. In addition, introduction of fusin and CD4 into a human cell line, U87MG, which is resistant to HIV-1 induced syncytium formation and to infection by HIV-1 when expressing CD4 alone made the cell line permissive for HIV Env-mediated cell—cell fusion. Fusion was observed with T-tropic Env proteins. Macrophage-tropic (M-tropic) Env proteins from the SF162, ADA, and Ba-L HIV-1 strains did not fuse with cells expressing fusin and CD4.

A second member of the seven-transmembrane domain protein family, the beta-chemokine receptor CKR-5 (alternately known as "CC-CKR5" or as "CCR-5"), mediates infection of macrophage by M-tropic HIV viruses. Co-expression of CKR-5 with CD4 enables nonpermissive cells to form syncytia with cells expressing M-tropic, but not T-tropic, HIV-1 env proteins. Expression of CKR-5 and CD4 permits entry of M-tropic, but not T-tropic, virus strain. See, Doranz et al. (1996) Cell 85 (7): 1149–58; Feng et al. (1996) Science 272 (5263): 872–7; Alkhatib et al. (1996) Science 272 (5270): 1955–8, and Deng et al. (1996) Nature 381 (6584): 661–6. Some T cells also express CKR-5 (e.g., in addition to fusin), and CKR-5 can also mediate infection of M-tropic HIV viruses into these T cells.

A dual-tropic primary HIV-1 isolate (89.6) utilizes both Fusin and CKR-5 as entry cofactors. See, Doranz et al., id. Cells expressing the 89.6 env protein form syncytia with QT6 cells expressing CD4 and either Fusin or CKR-5. The beta-chemokine receptors CKR-3 and CKR-2b support HIV-1 89.6 env-mediated syncytia formation but do not support fusion by any of the T-tropic or M-tropic strains tested. This indicates that the T-tropic viruses characteristic of disease progression may evolve from purely M-tropic viruses prevalent early in virus infection through changes in the env protein that enable the virus to use multiple entry cofactors.

SUMMARY OF THE INVENTION

A new strategy for inhibiting HIV infection of cells is provided herein. In the methods of the invention, mRNAs which encode HIV co-receptors from the 7-transmembrane receptor family are cleaved in cells, inhibiting expression of corresponding co-receptors on the surface of the cells. Because the level of co-receptor on the surface of the cell is reduced, HIV entry into the cells is inhibited. It is surprisingly discovered that clevage of HIV co-receptor mRNA using targeted ribozymes is not cytotoxic to cells expressing the co-receptor and that the cells retain normal immune function.

Accordingly, in one class of embodiments, the present invention provides endo-ribonuclease nucleic acids encoding ribozymes which cleave a co-receptor RNA expressed in a cell. These co-receptors are members of the seven transmembrane protein receptor family such as fusin and beta-chemokine receptors such as CKR-5, CKR-3 and CKR-2b. The endo-ribonuclease nucleic acids are ribozymes or nucleic acids (DNA or RNA, sense or complementary strand) which encode the ribozymes. Certain preferred co-receptor target subsequences are found in mRNAs encoding the receptor protein fusin, and a co-receptor RNA encoding the HIV co-receptor protein CKR5 (Sequence for the CKR5 receptor is found in GenBank at Accesion U57840. See also, Combadiere et al. (1996) J. Leukoc. Biol. 60 (1), 147–152 and Combadiere May 9, 1996 Direct Submission to GenBank). Preferred targets and ribozymes which cleave the targets are found in the sequence listings and examples described herein. Conservative modifications to the ribozyme and target sequences herein are obtained through routine optimization of the given sequences.

Typically, the ribozymes of the invention are hairpin ribozymes with a nucleic acid subsequence which is partially complementary to the target sequence to be cleaved. However, other ribozymes such as hammerhead and RNAase P ribozymes are also used. In addition, anti-sense molecules without catalytic activity are used to block expression of an RNA comprising a target subsequence, which subsequently can be cleaved by cellular RNase.

The endo-ribonuclease nucleic acids of the invention are optionally encoded in a vector for cellular or organismal transduction. In certain embodiments, the endo-ribonuclease nucleic acids are operably linked to a promoter. In some embodiments, it is desirable to express a ribozyme encoded by the end-ribonuclease nucleic acid at a high level. In these embodiments, a strong promoter such as a t-RNA or other pol III promoter is optionally used to direct expression of the ribozyme.

The ribozymes of the invention are used to cleave corresponding target nucleic acids both in vitro and in vivo. As described herein, in vitro cleavage reactions are used to monitor the presence of the corresponding target nucleic acid. In vivo cleavage (i.e., cleavage of a target by a ribozyme in a cell) renders the cell resistant to HIV infection.

A number of modifications to particular ribozymes described herein are made by optimizing the activity of the given ribozymes through routine modification. Modifications include increasing or decreasing the number of complementary nucleotides in helix 1, loop 3 nucleotide substitutions, helix 4 nucleotide substitutions, lengthening the helix 4 domain, shortening the helix 4 domain, lengthening the helix 3 domain, shortening the helix 3 domain, shortening the helix 1 domain, lengthening the helix 1 domain, adding DNA bases to the ribozyme, (e.g., during chemical synthesis or by enzymatic ligation) and conversion of the ribozyme to an RNA phosphothio analog.

In one class of embodiments, the invention provides methods of inhibiting HIV infection of a cell. In the methods, a co-receptor mRNA expressed in the cell is cleaved (e.g., using a hairpin ribozyme). The co-receptor is a member of the 7 transmembrane receptor family, such as fusin, CKR5, CKR-3 or CKR-2b. Cleavage of the co-receptor mRNA inhibits production of the selected co-receptor protein, thereby inhibiting HIV infection of the cell.

Fusin mediates HIV infection of T-tropic HIVs in T cells. Accordingly, in one embodiment, the cell in which infection is to be inhibited is a T cell and the co-receptor protein is fusin. Similarly, CKR5 mediates M-tropic HIV infection of macrophage. Accordingly, in one embodiment the cell is a macrophage cell and the co-receptor protein is CKR5. It will be appreciated that certain T cells comprise both fusin and CKR5, and that certain HIV strains are both T and M tropic. In these embodiments, the cell may be a T cell, and the co-receptor target is either CKR5 or Fusin, or both, and inhibition of the production of either CKR5 or fusin inhibits HIV infection of the cell.

In many embodiments, the co-receptor RNA to be cleaved is cleaved by one or more hairpin ribozymes of the invention expressed in the cell. Accordingly, in one class of embodiments, methods of the invention comprise transducing the cell to be protected with an endoribonuclease nucleic acid encoding a hairpin ribozyme which cleaves the co-receptor mRNA. A hairpin ribozyme can also be transduced into the cell, e.g., using vector targeted transduction, or using liposome-mediated nucleic acid delivery.

In certain "ex vivo" embodiments, the cell to be protected against HIV is isolated from a mammal susceptible to HIV. Typically, the mammal is already infected with HIV. In these methods, the cell is transduced with an endo-ribonuclease nucleic acid, e.g., in an expression vector, and re-introduced into the mammal. Often the cell is cultured or replicated prior to re-introduction to expand the number of transduced cells. Desirable cells for transformation include cells which are infected by HIV, i.e., $CD4^+$ cells, $fusin^+$ cells and $CKR5^+$ cells. Alternatively and preferably, hematopoietic stem cells (e.g., $CD34^+$ cells) which mature into HIV-infectable cells are transduced.

Kits comprising an endonuclease nucleic acid of the invention are also provided. Such kits typically include one or more of the following in addition to the endonuclease nucleic acid: a container, instructions in the use of the endoribonuclease nucleic acid, target nucleic acids (e.g., for use as positive controls to test the activity of the ribozyme) buffers, reagents, cells to be transduced with the endonuclease nucleic acids and the like.

DEFINITIONS

Figure 1:
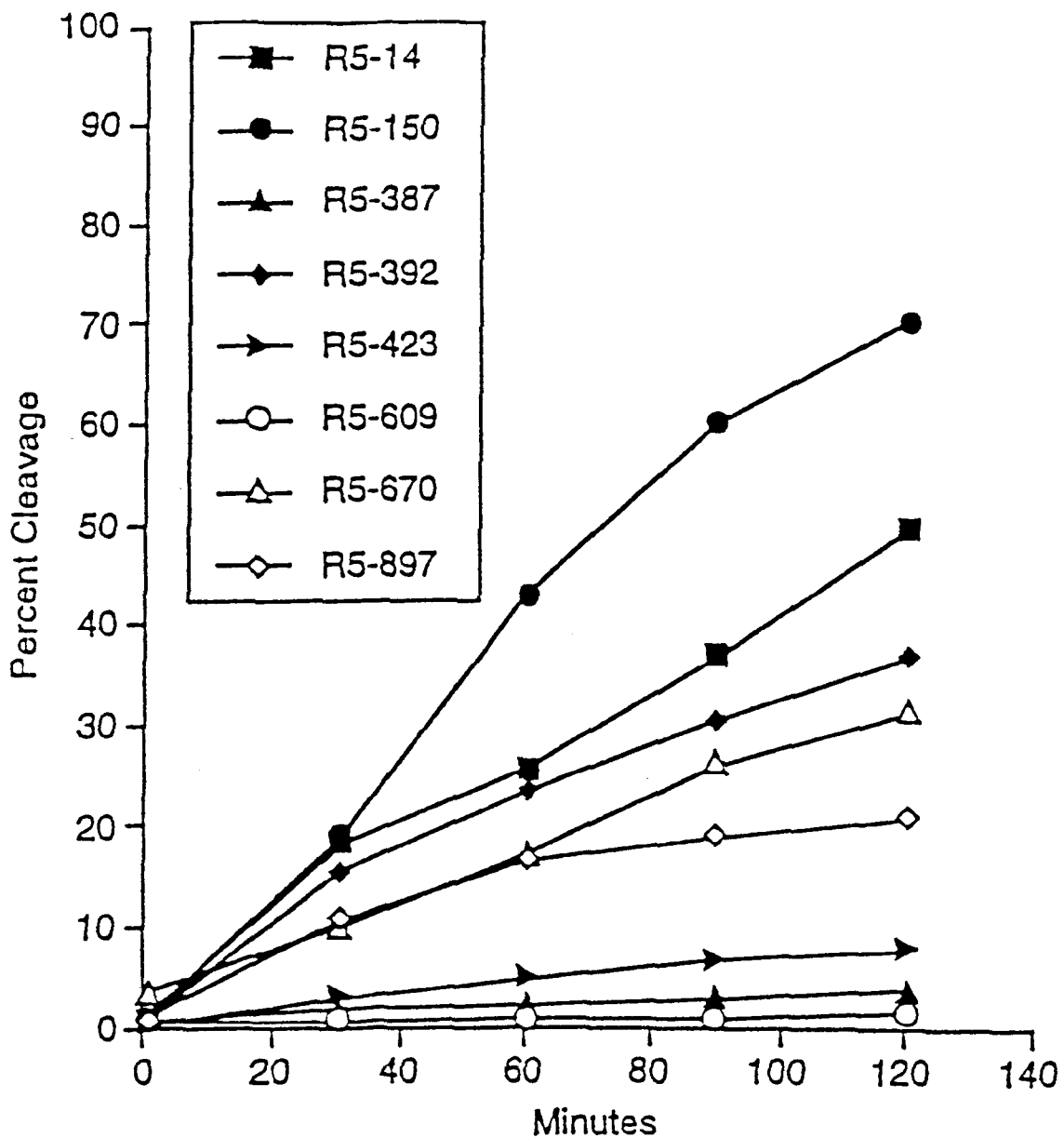
FIG. 1 is a graph showing the time course for clevage of CCR5 substrate RNAs by CCR5 Ribozymes.

For purposes of the present invention, the following terms are defined below.

An "endo-ribonuclease nucleic acid" is a nucleic acid which encodes a ribozyme which catalytically cleaves RNA. For example, the endo-ribonuclease nucleic acid is optionally a DNA encoding the ribozyme (either the sense or complementary strand). In another embodiment, the endo-ribonuclease nucleic acid is optionally an RNA which can be reverse transcribed into a DNA encoding the ribozyme. In yet another embodiment, the endo-ribonuclease nucleic acid is simply the ribozyme.

A "ribozyme" is a catalytic RNA molecule which cleaves RNA. The preferred class of ribozymes for the invention is the hairpin ribozyme. In particular, preferred hairpin ribozymes cleave target RNA molecules in trans. A ribozyme cleaves a target RNA in vitro when it cleaves a target RNA in solution. A ribozyme cleaves a target RNA in vivo when the ribozyme cleaves a target RNA in a cell. The cell is optionally isolated, or present with other cells, e.g., as part of a tissue, tissue extract, cell culture, or live organism. For example, a ribozyme is active in vivo when it cleaves a target RNA in a cell present in an organism such as a mammal, or when the ribozyme cleaves a target RNA in a cell present in cells or tissues isolated from a mammal, or when it cleaves a target RNA in a cell in a cell culture.

A "seven transmembrane protein" in the "seven transmembrane protein family" is a molecule expressed on the surface of a cell which has seven transmembrane domains through the cellular membrane. Examples include CKR5, Fusin, CKR-3 and CKR-2b.

A "GUC site" is an RNA subsequence found in an RNA molecule which includes the nucleic acids GUC. A "GUA site" is an RNA subsequence found in an RNA molecule which includes the nucleic acids GUA. A "target subsequence" includes a ribozyme cleavage site (e.g., GUC or GUA) and associated flanking sequence in a selected RNA.

A nucleic acid is "operably linked to a promoter" when there is a functional linkage between a nucleic acid expression control sequence (such as a promoter, or array of transcription factor binding sites) and a second nucleic acid sequence (such as a nucleic acid encoding a heterologous ribozyme nucleic acid), wherein the expression control sequence directs transcription (constitutive or inducible) of the nucleic acid corresponding to the second sequence in a cell.

An "expression vector" includes a recombinant expression cassette which has a nucleic acid which encodes an RNA that can be transcribed by a cell. A "recombinant expression cassette" is a nucleic acid subsequence of the construct, generated recombinantly or synthetically, with a series of specified nucleic acid elements which permit transcription of an encoded nucleic acid in a target cell. The expression vector can be part of a plasmid, virus, or nucleic acid fragment. Typically, the recombinant expression cassette portion of an expression vector includes a nucleic acid to be transcribed, and a promoter. In some embodiments, the expression cassette also includes, e.g., an origin of replication, and/or chromosome integration elements such as retroviral LTRs, or adeno associated viral (AAV) ITRs. A "promoter" is an array of nucleic acid control sequences which direct transcription of an associated nucleic acid. As used herein, a promoter optionally includes nucleic acid sequences near the start site of transcription, such as a polymerase binding site. The promoter also optionally includes distal enhancer or repressor elements which can be located as much as several thousand base pairs from the start site of transcription. A "constitutive" promoter is a promoter which is active under most environmental conditions and states of development or cell differentiation, such as a pol III promoter. An "inducible" promoter responds to an extracellular stimulus.

The term "recombinant" when used with reference to a cell indicates that the cell replicates or expresses a nucleic acid, or expresses a peptide or protein encoded by a nucleic acid whose origin is exogenous to the cell. Recombinant cells can express nucleic acids that are not found within the native (non-recombinant) form of the cell. Recombinant cells can also express genes found in the native form of the cell, wherein the genes are re-introduced into the cell by artificial means, for example under the control of a heterologous promoter.

The term "heterologous" when used with reference to a nucleic acid indicates that the nucleic acid comprises two or more subsequences which are not found in the same relationship to each other in nature. For instance, the nucleic acid is typically recombinantly produced, having two or more sequences derived from unrelated genes arranged to make a new functional nucleic acid. For example, in one embodiment, the nucleic acid has a promoter from one gene, such as a human t-RNA gene, arranged to direct the expression of a coding sequence from a different gene, such as an artificial gene coding for a ribozyme. When used with reference to a ribozyme, the term "heterologous" means that the ribozyme is man made, or expressed in a cell or location where it is not ordinarily expressed in nature, such as in a T cell which encodes the ribozyme in an expression cassette.

The term "subsequence" in the context of a particular nucleic acid refers to a region of the nucleic acid equal to or smaller than the particular nucleic acid or polypeptide.

A "pol III promoter" is a DNA sequence competent to initiate transcription of associated DNA sequences by pol III. Many such promoters are known, including those which direct expression of known t-RNA genes. Various pol III promoters are described in Watson et al. *Molecular Biology of The Gene* Fourth Edition, The Benjamin Cummings Publishing Co., Menlo Park, Calif. pages 710–713.

A "helix 1" ribozyme domain is the portion of a nucleic acid encoding the ribozyme which is complementary to a target RNA 3' of the cleavage site on the target RNA, i.e., the ribozyme nucleic acid sequences 5' of the ribozyme nucleic acid subsequence which aligns with the target cleavage site.

A vector "transduces" a cell when it transfers nucleic acid into the cell. A cell is "stably transduced" by a nucleic acid when a nucleic acid transduced into the cell becomes stably replicated by the cell, either by incorporation of the nucleic acid into the cellular genome, or by episomal replication.

DETAILED DESCRIPTION OF THE INVENTION

Several HIV co-receptors have been identified, including fusin, CKR-5, and the beta-chemokine receptors CKR-3 and CKR-2b. In the methods of the invention, expression of these HIV receptors is inhibited, thereby inhibiting infection of the cells by HIV. Inhibition of expression is achieved by blocking translation of the mRNA molecules which encode the HIV co-receptor proteins. This is accomplished by cleaving the mRNA in vivo, i.e., using a ribozyme which catalytically cleaves the mRNA, or by expressing an antisense molecule which binds to the mRNA and inhibits translation of the mRNA.

Ribozymes, RNA and DNA molecules encoding the ribozymes and ribozyme targets in the co-receptor mRNAs are provided. A ribozyme is a catalytic RNA molecule that cleaves other RNA molecules having nucleic acid sequences that are complementary to particular targeting sequences in the ribozyme. Castanotto et al (1994) *Advances in Pharmacology* 25: 289–317 provides and overview of ribozymes in general, including group I ribozymes, hammerhead ribozymes, hairpin ribozymes, RNAse P, and axhead ribozymes.

Hairpin ribozymes, which are preferred for use in the methods of the invention, are catalytic RNA molecules with RNA endonuclease activity. The hairpin ribozyme was originally derived from the 359 bases of the negative strand of the satellite RNA of tobacco ringspot virus. The hairpin ribozyme is catalytic, cleaving target RNA to produce a 5' fragment terminating in a 2',3' cyclic phosphate and a 3' fragment bearing a newly formed 5'-OH. The reaction is reversible, forming a normal phosphodiester bond. See generally, Buzayan, et al. *Nature,* 323: 349–352 (1986); Gerlach, et al., (1986) *Virology,* 151: 172–185; Hampel et al (1989) *Biochemistry,* 28: 4929–4933; Gerlach et al., (1989) *Gene,* 82: 43–52; Feldstein et al., (1989) *Gene,* 82: 53–61; and Hampel et al. Australian Patent No. AU-B-41594/89.

General features of hairpin ribozymes are also described e.g., in Hampel et al. (1990) *Nucl. Acids Res.* 18:299–304; Hampel et al., (1990) European Patent Publication No. 0 360 257; U.S. Pat. No. 5,254,678, issued Oct. 19, 1993; Wong-Staal et al., WO 94/26877; Yu et al. (1993) *Proc Natl Acad Sci USA* 90:6340–6344; Yamada et al. (1994) *Human Gene Therapy* 1:39–45, Yu et al. (1995) *Proc Natl Acad Sci USA* 92:699–703; Leavitt et al. (1994) *Human Gene Therapy* 5:1151–1120; and Yamada et al. (1994) *Virology* 205:121–126.

Intracellular expression of certain hairpin ribozymes directed against HIV RNA has been shown to confer significant resistance to HIV infection. In the present invention, intracellular expression of the ribozymes of the invention inhibits the expression of HIV co-receptor RNA, thereby inhibiting the expression of HIV co-receptor proteins on the surface of the cell. By blocking the expression of these proteins which mediate HIV infection of cells, the cells are rendered resistant to HIV infection.

Hairpin ribozymes typically cleave one of two target sequences. GUC ribozymes cleave an RNA target sequence consisting of NNNBN*GUCNNNNNNNN (SEQ ID NO: 1) (where N*G is the cleavage site, B is any of G, U or C, and where N is any of G, U, C, or A). GUA ribozymes typically cleave an RNA target sequence consisting of NNNNN*GUANNNNNNNN. (SEQ ID NO: 2) (where N*G is the cleavage site and where N is any of G, U, C, or A). See, De Young et al. (1995) *Biochemistry* 34: 15785–15791. Cleavage sites in the mRNA of HIV co-receptors are identified based on the presence of the hairpin cleavage site BNGUC, in the target RNA. For example, the coding sequence of CKR-5 contains 18 BNUGC (SEQ ID NO: 3) sites. Thus, there are 18 hairpin ribozyme target sites present in the protein coding region of the CCR5 mRNA corresponding to the consensus target site BNGUC (SEQ ID NO: 3).

Preferred cleavage sites are selected based on the criteria that helix 2 of the bound ribozyme contain at least two GC base pairs. The catalytic activity of each of ribozymes binding to the preferred cleavage sites is assessed by the following a time course for the cleavage reaction. Cleavage reactions are performed at a substrate to ribozyme ratio of about 13.5:1. The reactions are incubated at 30° C. for 2 hr with time points being taken, e.g., at 0, 30, 60, 90, and 120 min. The products of the reaction are resolved, e.g., by urea PAGE and the extent of cleavage quantitated, e.g., on a Molecular Dynamics phosphorimager. The ribozymes which show the greatest level of activity during the time course are further analyzed by determining the catalytic efficiency for these ribozymes. The catalytic efficiency is defined as kcat/Km. Activity of the ribozymes is confirmed in tissue culture by challenge of vector transduced cells with HIV.

Making Ribozymes and Target Nucleic acids

RNA and DNA nucleic acids, including ribozymes, nucleic acids encoding ribozymes, ribozyme targets, and nucleic acids encoding ribozyme targets, can be synthesized chemically according to known methods such as the solid phase phosphoramidite triester method described by Beaucage and Caruthers (1981), *Tetrahedron Letts.,* 22(20) :1859–1862, e.g., using an automated synthesizer, as described in Needham-VanDevanter et al. (1984) *Nucleic Acids Res.,* 12:6159–6168. Purification of the molecules, where necessary, is typically performed by either gel electrophoresis or by anion-exchange HPLC as described in Pearson and Regnier (1983) *J. Chrom.* 255:137–149. The sequence of the synthetic DNA and RNA molecules can be verified using the chemical degradation method of Maxam and Gilbert (1980) in Grossman and Moldave (eds.) Academic Press, New York, *Methods in Enzymology* 65:499–560. Alternatively, the molecules can be cloned into an appropriate sequencing vector and sequenced using standard dideoxy sequencing methods.

Ribozymes optionally comprise non-standard ribonucleotide bases, or deoxyribonucleotide bases, which can stabilize the ribozyme and make it resistant to RNase enzymes. Alternatively, the ribozyme can be modified to the phosphothio analog for use in liposome delivery systems. This modification also renders the ribozyme resistant to endonuclease activity.

Alternatively, ribozymes are prepared from a DNA molecule, e.g., comprising an expression cassette that, upon transcription, yields a ribozyme of the invention. An expression cassette of the invention comprises a promoter sequence (e.g., a polymerase II promoter, a polymerase III promoter, or the like) operably linked to a sequence encoding the ribozyme.

Various promoters can be used to direct expression of the ribozymes of the invention, depending on the application. Typically, expression of the construct is high enough to inhibit the growth, infection or replication of the virus (e.g., HIV) against which protection is sought. Accordingly, strong promoters are useful for directing expression of the ribozymes. Such promoters include, but are not limited to, pol III promoters such as the U1, 5S RNA and t-RNA promoters (e.g., the human tRNA$^{val}$ promoter; see, Wong-Staal et al. WO 94/26877); strong constitutive cellular promoters known to persons of skill, including the U1 promoter, the β-actin promoter and the tubulin promoter; viral pol II promoters such as SV 40 promoters and RSV LTR promoters, and tissue specific promoters such as CD4-specific promoters. A CD4$^+$ specific promoter is a promoter which directs high levels of expression in CD4$^+$ cells, but not in unrelated cell types. Examples of CD4-specific promoters include the promoters for the human and murine CD4 receptor genes, which are known in the art. For example, Solomon et al. (1993) *Proc. Natl. Acad. Sci. USA* 90:7739–7743 describes the characterization of the human CD4 gene promoter.

General cloning methodologies to produce nucleic acids which encode ribozymes or ribozyme targets of the invention are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

The nucleic acid compositions of this invention, whether RNA, DNA, cDNA, genomic DNA, genomic RNA or a hybrid of the various combinations, are isolated from natural sources, cloned heterologous sources, or synthesized in vitro. The nucleic acids claimed are present in transduced or transfected whole cells, in transduced or transfected cell lysates, or in a partially purified or substantially pure form.

In vitro amplification techniques are suitable for amplifying RNA or DNA sequences for use as molecular probes, RNA endonucleases (i.e., where the RNA is a ribozyme) or generating nucleic acids for subsequent subcloning. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Making Ribozymes Based on Those in the Sequence Listings.

Once a target RNA is identified (e.g., by virtue of a GUC or GUA), and a ribozyme is constructed which cleaves the target in vivo, one of skill can generate many similar targets and ribozymes by performing routine modification of the given targets and ribozymes. Such routinely modified ribozymes are "conservative modifications" of a particular ribozme. For instance, lengthening or shortening the helix 1 or helix 2 domain of the ribozyme can have an effect on the activity of the ribozyme. See, Anderson et al. (1994) Nucleic Acids Research 22(6): 1096–1100. Thus, for each of the ribozymes in the sequence listings herein, one of skill will readily recognize that many ribozymes consist essentially of the given sequence, differing only by the number of nucleotides complementary to the target RNA in the helix 1 or helix 2 domains of the ribozyme. Preferred ribozymes have a helix one length of from about 4 to about 20 bases complementary to a nucleotides flanking the cleavage site. For example, in one class of embodiments, helix 1 has about 6 to about 12 complementary nucleotides. Specific ribozymes with specific helix 1 lengths are described in the examples below. Other conservative modifications include lengthening helix 3 and helix 4 regions, reversing the position of individual complementary nucleotides in the helices and substituting loop 3 domain nucleotides. In addition, the target binding sequence can be altered to hybridize to allelic variants of the given target sequences.

Similarly, one of skill will understand that the target sequences given in the sequence listings can be depicted as the given sequence, or as the given sequence plus additional flanking sequence, or with some of the nucleotides flanking the cleavage site deleted. Such different depictions do not change the essential nature of the target site, and it is understood that alternately represented target sites consist essentially of the given targets. In addition, the target can be modified by the substitution of one or a few nucleotides in the target. For example, allelic variants which encode changes in helix 1 and/or helix 2 binding sites can be cleaved by ribozymes which have compensatory changes in helix 1 or helix 2.

Thus, the ribozymes in the sequence listing are optionally modified by making loop 3 nucleotide substitutions, helix 4 nucleotide substitutions, lengthening or shortening the helix 4 domain, lengthening or shortening the helix 3 domain, or lengthening or shortening the helix 1 or helix 2 domain. Furthermore, as described above, the ribozymes of the sequence listing and examples can be modified by synthetic incorporation of non-standard ribonucleotides or deoxyribonucleotides and/or conversion of the ribozyme to an RNA phosphothio analog. One of skill will readily appreciate that such minor modification of the given ribozymes is possible, and that the methods of making and screening the modifications is straightforward, and is performed by adapting the ribozymes described herein. Accordingly, it will immediately be recognized that each ribozyme in the sequence listings can be modified in a variety of ways to yield similar ribozymes with similar or identical activity.

In one preferred embodiment, stabilizing elements are incorporated into the expressed ribozyme to increase the stability of the ribozyme. For instance, the HIV rev response element (RRE) which stabilizes HIV transcripts (or a minimal Rev binding sequence thereof) is optionally incorporated into the ribozyme to stabilize the ribozyme. See, Wong-Staal et al. (1991) "Viral And Cellular Factors that Bind to the Rev Response Element" in *Genetic Structure and Regulation of HIV* (Haseltine and Wong-Staal eds.; part of the Harvard AIDS Institute Series on Gene Regulation of Human Retroviruses, Volume 1), pages 311–322 and the references cited therein. Another example of an RNA stabilizing element is the 340 bp insert from the Mason Pfizer Monkey Virus (MPMV) which targets nucleic acids to the cytosol. See, Bray et al. (1994) *Proc. Natl. Acad. Sci. USA* 91: 1256–1260.

In other embodiments, the target binding sequence is altered to match homologous sites on allelic variants of the co-receptor mRNAs. The identification of a target cleaved by a ribozyme in vitro and in vivo, and the sequence of a ribozyme which cleaves the target provides one of skill with information sufficient for constructing structurally similar ribozymes that cleave the identified target.

In Vitro Uses For the Ribozymes of the Invention

The ribozymes of the invention are generally useful for their endoribonuclease activity. The ability to specifically cleave RNAs in vitro is used to prepare RNAs for cloning, e.g., prior to reverse transcription into cDNA and cloning. For example, an RNA which comprises a target subsequence can be cleaved by an appropriate ribozyme to yield two RNAs. The RNAs can then be cloned for further analysis. Thus, ribozymes provide a commercially valuable tool useful in recombinant construction of nucleic acids. Tools which perform similar functions, such as DNA endonucleases (restriction enzymes), are widely used and highly valuable.

The ability to cleave target RNA in vitro also provides an assay for the presence or availability of the RNA target site. For instance, HIV co-receptor RNA comprising a specified target subsequence can be detected by cleaving the RNA with a ribozyme and detecting the resulting fragments with an appropriate probe or probes. Sambrook and Ausbel, both supra, describes methods of detecting RNAs, such as northern blotting.

In addition to chemical synthesis of the ribozymes, the ribozymes are also made by cloning DNA encoding the ribozymes into known expression systems in vitro, and in various cell cultures such as bacteria, yeast, mammalian cells, plants and the like, and purifying the ribozymes using standard techniques for RNA isolation. Sambrook, Ausbel and Berger, all supra, provide an introduction to gene expression systems.

Ribozymes are typically active in vitro, e.g., in tris-based buffers containing $Mg^{++}$ and optionally other salts. Spermidine is also added to many in vitro buffers. For instance, one typical in vitro buffer for assaying ribozyme activity is 40 mM Tris-HCl pH 7.5, 10 mM $MgCl_2$ and 2 mM spermidine.

In Vivo Uses for the Ribozymes of the Invention: Preferred Cell Transduction Vectors In preferred embodiments, the cellular expression of the ribozymes of the invention inhibits infection of cells by HIV. This property is useful in cell and tissue culture, where inadvertent infection of cells by HIV is dangerous to people handling the cells. In more preferred embodiments, the ability of the ribozymes of the invention to inhibit HIV infection is used to inhibit or ameliorate HIV infection in a patient.

Vectors exist for the delivery of transcription cassettes comprising the ribozymes of the invention in organismal in vivo procedures and in ex vivo procedures. Examples of vectors include those described in Wong-Staal et al., WO 94/26877; Sullenger et al. (1990) *Molecular and Cellular Biology* 10(12): 6512–6523; Gilboa et al. (PCT publication WO 90/13641, and Chatterjee et al. (1992) *Science* 258: 1485–1487.

Vectors are targeted by a variety of means known in the art. In one preferred class of embodiments, the vectors of the invention include retroviral particles. These particles are typically specific for cell types within the host range of the retrovirus from which the particle is derived. For example, HIV infects $CD4^+$ cells; accordingly, in one embodiment, the vectors of the invention comprise an HIV particle, permitting the vector to be transduced into $CD4^+$ cells, in vitro, ex vivo or in vivo. Vectors comprising HIV particles can also be used to transduce non-dividing hematopoietic stem cells ($CD34^+$), by pseudotyping the vector. $CD34^+$ cells are a good target cells for ex vivo gene therapy, because the cells differentiate into many different cell types, and because the cells re-engraft into a patient undergoing ex vivo therapy. The vesicular stomatitis virus envelope glycoprotein (VSV-G) has been used to construct VSV-G-pseudotyped HIV vectors which can infect hematopoietic stem cells (Naldini et al. (1996) Science 272:263 and Akkina et al. (1996) *J Virol* 70:2581). Additional methods of transferring nucleic acids into $CD34^+$ hematopoietic progenitor cells are described in Brenner (1993) *Journal of Hematotherapy* 2: 7–17.

In addition to viral particles, a variety of protein coatings can be used to target nucleic acids to selected cell types. Transferrin-poly-cation conjugates enter cells which display transferrin receptors. See, e.g., Zenke et al (1990) *Proc. Natl. Acad. Sci. USA* 87: 3655–3659; Curiel (1991) *Proc. Natl. Acad Sci USA* 88: 8850–8854 and Wagner et al. (1993) *Proc. Natl. Acad. Sci. USA* 89:6099–6013.

Naked plasmid DNA bound electrostatically to poly-1-lysine or poly-1-lysine-transferrin which has been linked to defective adenovirus mutants can be delivered to cells with transfection efficiencies approaching 90% (Curiel et al. (1991) *Proc Natl Acad Sci USA* 88:8850–8854; Cotten et al. (1992) *Proc Natl Acad Sci USA* 89:6094–6098; Curiel et al. (1992) *Hum Gene Ther* 3:147–154; Wagner et al. (1992) *Proc Natl Acad Sci USA* 89:6099–6103; Michael et al. (1993) *J Biol Chem* 268:6866–6869; Curiel et al. (1992) *Am J Respir Cell Mol Biol* 6:247–252, and Harris et al. (1993) *Am J Respir Cell Mol Biol* 9:441–447). The adenovirus-poly-1-lysine-DNA conjugate binds to the normal adenovirus receptor and is subsequently internalized by receptor-mediated endocytosis. Similarly, other virus-poly-1-lysine-DNA conjugates bind the normal viral receptor and are subsequently internalized by receptor-mediated endocytosis. Accordingly, a variety of viral particles can be used to target vector nucleic acids to cells.

Other receptor-ligand combinations which can be used to target DNA which is complexed to the ligand to a cell include cytokines and cytokine receptors, interleukins and interleukin receptors, c kit and the c kit receptor (see, Schwartzenberger et al (1996) *Blood* 87: 472–478), antibodies and cell surface molecules, and the like.

In addition to, or in place of receptor-ligand mediated transduction, the vector nucleic acids of the invention are optionally complexed with liposomes to aid in cellular transduction. Liposome based gene delivery systems are described in Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414.

Organismal cellular transduction provides methods for combating chronic infectious diseases such as AIDS, caused by HIV infection, as well as non-infectious diseases such as cancer. Yu et al. (1994) *Gene Therapy* 1:13–26 and the references therein provides a general guide to gene therapy strategies for HIV infection. See also, Sodoski et al. PCT/US91/04335. Wong-Staal et al., WO/94/26877 describe retroviral gene therapy vectors.

Common organismal cellular transduction vectors include, but are not limited to, those derived from murine retroviruses (including MoMLv), avian rous sarcoma virus (RSV), Hepatocyte viruses, HIV-1, HIV-2, and adeno-associated virus (AAV)-based vectors.

The majority of the approved gene transfer trials in the United States rely on replication-defective murine retroviral vectors harboring a therapeutic polynucleotide sequence as part of the retroviral genome (Miller et al. *Mol. Cell. Biol.* 10:4239 (1990); Kolberg R *J. NIH Res.* 4:43 (1992); Cornetta et al. *Hum. Gene Ther.* 2:215 (1991)). Murine retroviral vectors have been used to stably introduce ribozyme genes into target cells, and similar approaches can be used for the ribozymes of the invention. See, Yamada et al. (1994) *Gene Therapy* 1:38–45.

AAVs utilize helper viruses such as adenovirus or herpes virus to achieve productive infection. In the absence of helper virus functions, wild-type AAV integrates (site-specifically) into a host cell's genome, but the integrated AAV genome has no known pathogenic effect. The integration step allows the AAV genome to remain genetically intact until the host is exposed to the appropriate environmental conditions (e.g., a lytic helper virus), whereupon it re-enters the lytic life-cycle. Samulski (1993) *Current Opinion in Genetic and Development* 3:74–80 and the references cited therein provides an overview of the AAV life cycle. For a general review of AAVs and of the adenovirus or herpes helper functions see, Berns and Bohensky (1987) *Advanced in Virus Research*, Academic Press., 32:243–306. The genome of AAV is described in Laughlin et al. (1983) *Gene*, 23:65–73. Expression of AAV is described in Beaton et al. (1989) *J. Virol.*, 63:4450–4454.

AAV-based vectors are used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.*, 4:2072–2081; Hermonat and Muzyczka (1984) *Proc. Natl. Acad. Sci. USA*, 81:6466–6470; McLaughlin et al. (1988) and Samulski et al. (1989) *J. Virol.*, 63:03822–3828. Cell lines that can be transduced by rAAV include those described in Lebkowski et al. (1988) *Mol. Cell. Biol.*, 8:3988–3996.

Recombinant AAV vectors (rAAV vectors) deliver foreign nucleic acids to a wide range of mammalian cells (Hermonat & Muzycka (1984) *Proc Natl Acad Sci USA* 81:6466–6470; Tratschin et al. (1985) *Mol Cell Biol* 5:3251–3260), integrate into the host chromosome (Mclaughlin et al. (1988) *J Virol* 62: 1963–1973), and show stable expression of the transgene in cell and animal models (Flotte et al. (1993) *Proc Natl Acad Sci USA* 90:10613–10617). rAAV vectors are able to infect non-dividing cells (Podsakoff et al. (1994) *J Virol* 68:5656–66; Flotte et al. (1994) *Am. J. Respir. Cell Mol. Biol.* 11:517–521). Further advantages of rAAV vectors include the lack of an intrinsic strong promoter, thus avoiding possible activation of downstream cellular sequences, and the vector's naked icosohedral capsid structure, which renders the vectors stable and easy to concentrate by common laboratory techniques.

rAAV vectors are used to inhibit, e.g., viral infection, by including antiviral transcription cassettes in the rAAV vector. For example, Chatterjee et al. (*Science* (1992), 258: 1485–1488) describe anti-sense inhibition of HIV-1 infectivity in target cells using an rAAV vector with a constitutive expression cassette expressing anti-TAR RNA. Chatterjee et al. (PCT application PCT/US91/03440 (1991), hereinafter Chatterjee et al. 2) describe rAAV vectors, including rAAV vectors which express antisense TAR sequences. Chatterjee and Wong (*Methods, A companion to Methods in Enzymology* (1993), 5: 51–59) further describe rAAV vectors for the delivery of antisense RNA. These known vectors can be modified by substituting the anti-sense sequences in the vectors with the ribozymes of the invention.

HIV based vectors and AAV based vectors are used for transduction of CD4$^+$ cells, because they do not require actively dividing cells for transduction (unlike murine retroviruses). In some applications, HIV vectors are used, because they typically only infect CD4$^+$ cells in an organism, i.e., those cells which are infected by HIV viruses.

When using retroviral vectors, packaging cells are commonly used to prepare the virions used to transduce the target cells. In these cells, trans active genes rendered inactive in a gene therapy vector are "rescued" by trans complementation to provide a packaged vector. For instance, cells transduced with HIV or murine retroviral proviral sequences which lack the nucleic acid packaging site produce retroviral trans active components, but do not specifically incorporate the retroviral nucleic acids into the capsids produced, and therefore produce little or no live virus. When these transduced "packaging" cells are subsequently transduced or transfected with a vector nucleic acid which lacks coding sequences for retroviral trans active functions, but includes sequences necessary for packaging, reverse transcription and integration, the vector nucleic acid is packaged into an infective virion. A number of packaging cell lines useful for MoMLV-based vectors are known in the art, such as PA317 (ATCC CRL 9078) which expresses MoMLV core and envelope proteins see, Miller et al. (1991) *J. Virol.* 65:2220–2224. Carrol et al. (1994) *Journal of virology* 68(9):6047–6051 describe the construction of packaging cell lines for HIV viruses.

Functions of viral replication not supplied by trans-complementation which are necessary for transduction of the vector are present in the vector. For HIV based vectors, this typically includes, e.g., the TAR sequence, the sequences necessary for HIV packaging, the RRE sequence if the instability elements of the p17 gene of gag is included, and sequences encoding the polypurine tract. HIV sequences that contain these functions include a portion of the 5' long terminal repeat (LTR) and sequences downstream of the 5' LTR responsible for efficient packaging, i.e., through the major splice donor site ("MSD"), and the polypurine tract upstream of the 3' LTR through the U3R section of the 3' LTR. The packaging site (psi site or ψ site) is located adjacent to the 5' LTR, primarily between the MSD site and the gag initiator codon (AUG) in the leader sequence. See, Garzino-Demo et al. (1995) *Hum. Gene Ther.* 6(2): 177–184. For a general description of the structural elements of the HIV genome, see, Holmes et al. PCT/EP92/02787.

The present invention provides several features that allow one of skill to generate powerful gene therapy vectors (including, but not limited to AAV vectors, HIV vectors and RSV vectors) against specific cellular targets, in vitro and in vivo, e.g., against $CD4^+$ cells. For example, $CD4^+$ cells are infected by HIV viruses (provided appropriate co-receptor are present), and transduced by HIV-based vectors. Lists of $CD4^+$ and CD4– cell types which are infectable by HIV have been compiled (see, Rosenburg and Fauci 1 supra; Rosenburg and Fauci (1989) *Adv Immunol* 47:377–431; and Connor and Ho (1992) in *AIDS: etiology, diagnosis, treatment, and prevention,* third edition Hellman and Rosenburg (eds) Lippincott, Philadelphia).

In addition to $CD4^+$ cells, transduction of $CD34^+$ hematopoietic stem cells by vectors encoding the ribozymes of the invention is also highly desirable. These stem cells differentiate into a variety of immune cells, including $CD4^+$ cells which are the primary targets for HIV infection. $CD34^+$ cells are the most important target cells for ex vivo gene therapy, because these cells differentiate into many different cell types, and because the cells are capable of re-engraftment into a patient undergoing ex vivo therapy.

HIV-based vectors are made competent to transduce $CD34^+$ cells by pseudotyping the vector. This is done by transducing the packaging cell line used to package the vector with a nucleic acid which encodes the vesicular stomatitis virus (VSV) envelope protein, which is then expressed on the surface of the HIV vector. VSV infects $CD34^+$ cells, and pseudotype vectors expressing VSV envelope proteins are competent to transduce these cells.

Nucleic acids encoding ribozymes of the invention are useful as components of gene therapy vectors. Retroviral vectors packaged into HIV envelopes primarily infect $CD4^+$ cells, (i.e., by interaction between the HIV envelope glycoprotein and the CD4 "receptor") including, non-dividing $CD4^+$ cells such as macrophage. For instance, nucleic acids which encode ribozymes are encapsidated into HIV capsids in gene therapy vectors which include an HIV packaging site (e.g., the ψ site in HIV, see, Aldovini and Young (1990) *Journal of Virology* 64(5):1920–1926, and Clever et al. (1995) *Journal of Virology* 69(4): 2101–2109), and typically also include the HIV LTR sequences. Thus, in one embodiment, the ribozymes of the present invention are incorporated into HIV-based gene therapy vectors which deliver the ribozymes to $CD4^+$ or $CD34^+$ cells. This is accomplished by incorporating cis active nucleic acids (e.g., promoter sequences, packaging sequences, integration or cellular targeting sequences) into the vector, or by using trans active nucleic acids and polypeptides (capsid and envelope proteins and transcription factors) to replicate and package the gene therapy vector into an viral capsid (e.g., an HIV capsid and envelope), or both. See, e.g., Poznansky et al. (1991) *Journal or Virology* 65(1): 532–536 and Garzino Demo et al. (supra) for a description of the of the region flanking the 5' HIV LTR.

Ex Vivo Transduction of Cells

Ex vivo methods for inhibiting viral replication in a cell in an organism involve transducing the cell ex vivo with a therapeutic nucleic acid of this invention, and introducing the cell into the organism. The cells are typically $CD4^+$ cells such as $CD4^+$ T cells or macrophage isolated or cultured from a patient, or are hematopoietic stem cells. Alternatively, the cells can be those stored in a cell bank (e.g., a blood bank).

In one class of embodiments, the vector is replicated and packaged into HIV capsids using the HIV replication machinery, thereby causing the anti-HIV ribozyme to propagate in conjunction with the replication of an HIV virus. Thus, an organism infected with HIV can be treated for the infection by transducing a population of its cells with a vector of the invention and introducing the transduced cells back into the organism as described herein. Thus, the present invention provides compositions and methods for protecting cells in culture, ex vivo and in a patient.

The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells. Transduced cells are cultured by means well known in the art. See, also Kuchler et al. (1977) *Biochemical Methods in Cell Culture and Virology,* Kuchler, R. J., Dowden, Hutchinson and Ross, Inc. Mammalian cell systems often will be in the form of monolayers of cells, although mammalian cell suspensions are also used. Illustrative examples of mammalian cell lines include VERO and Hela cells, Chinese hamster ovary (CHO) cell lines, W138, BHK, Cos-7 or MDCK cell lines (see, e.g., Freshney, supra).

In one embodiment, $CD34^+$ stem cells (which are typically not $CD4^+$) are used in ex-vivo procedures for cell transduction and gene therapy. The advantage to using stem cells is that they can be introduced into a mammal (such as the donor of the cells) where they will engraft in the bone marrow.

In humans, CD34 cells can be obtained from a variety of sources including cord blood, bone marrow, and mobilized peripheral blood. Purification of CD34+cells can be accomplished by antibody affinity procedures. Wong-Staal et al. WO 94/26877 describe methods of isolating and transforming $CD34^+$ cells. An affinity column isolation procedure for isolating $CD34^+$ cells is described by Ho et al. (1995) *Stem Cells* 13 (suppl. 3): 100–105. See also, Brenner (1993)

*Journal of Hematotherapy* 2: 7–17. Yu et al. (1995) *PNAS* 92: 699–703 describe a method of transducing CD34+cells from human fetal cord blood using retroviral vectors.

Rather than using stem cells, T cells or macrophage are also used in some embodiments in ex vivo procedures. Several techniques are known for isolating T cells. One procedure for isolating T cells is described in Leavitt et al. *Hum. Gene Ther.* (1994) 5:1115–1120. Wong-Staal et al. WO 94/26877 also describes methods of isolating and transforming T cells. HIV inhibitors are typically added to cultures of T-cells to inhibit HIV growth when the T cells are isolated from potentially HIV-positive sources. For example, delaviridine can be added to cultures of T cells at a concentration of from about 1 to about 10 $\mu$M to inhibit HIV growth.

The expression of surface markers facilitates identification and purification of T cells and macrophage. Methods of identification and isolation of T cells and macrophage include FACS, incubation in flasks with fixed antibodies which bind the particular cell type and panning with magnetic beads.

Administration of Vectors and Transduced Cells

Vectors comprising endo-ribonuclease nucleic acids can be administered directly to a patient for transduction of cells in the patient. Administration is by any of the routes normally used for introducing a molecule into ultimate contact with blood or tissue cells. Vector packaged nucleic acids encoding the ribozymes of the invention are administered in any suitable manner, preferably with pharmaceutically acceptable carriers. Alternatively, the nucleic acids (e.g., ribozymes) can be naked, or present in a liposome. Suitable methods of administering such nucleic acids in the context of the present invention to a patient are available.

Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are suitable methods of administration. The formulations of packaged nucleic acid can be presented in unit-dose or multi-dose sealed containers, such as ampules and vials.

The dose administered to a patient, in the context of the present invention should be sufficient to effect a beneficial therapeutic response in the patient over time, or to inhibit infection by a pathogen. The dose will be determined by the efficacy of the particular vector employed and the condition of the patient, as well as the body weight or surface area of the patient to be treated. The size of the dose also will be determined by the existence, nature and extent of any adverse side-effects that accompany the administration of a particular vector, or transduced cell type in a particular patient.

In determining the effective amount of the vector to be administered in the treatment or prophylaxis of virally-mediated diseases such as AIDS, the physician evaluates circulating plasma levels, vector and ribozyme toxicities, progression of the disease, and the production of anti-vector antibodies.

For administration, ribozymes and transduced cells of the present invention can be administered at a rate determined by the LD-50 of the ribozyme, vector, or ribozyme-transduced cell type, and the side-effects of the ribozyme, vector or cell type at various concentrations, as applied to the mass and overall health of the patient. Administration can be accomplished via single or divided doses.

Transduced cells are prepared for reinfusion according to established methods. See, Abrahamsen et al. (1991) *J. Clin. Apheresis* 6:48–53; Carter et al. (1988) *J. Clin. Apheresis* 4:113–117; Aebersold et al. (1988), *J. Immunol. Methods* 112: 1–7; Muul et al. (1987) *J. Immunol. Methods* 101:171–181 and Carter et al. (1987) *Transfusion* 27:362–365. In one class of ex vivo procedures, between $1 \times 10^6$ and $1 \times 10^9$ transduced cells (e.g., stem cells or T cells transduced with vectors encoding the ribozymes of the invention) are infused intravenously, e.g., over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion may be repeated about every 2 to 3 months for a total of 4 to 6 treatments in a one year period. After the first treatment, infusions can be performed on a outpatient basis at the discretion of the clinician.

If a patient undergoing infusion of a vector or transduced cell develops fevers, chills, or muscle aches, he/she typically receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion is slowed or discontinued depending upon the severity of the reaction.

The effect of the therapeutic vectors, ribozymes, or transduced cells of the invention on HIV infection and AIDS are measured by monitoring the level of HIV virus in a patient, or by monitoring the CD4$^+$ cell count for the patient over time. Typically, measurements are taken before, during and after the therapeutic regimen. Kits for detecting and quantitating HIV and CD4$^+$ cells are widely available. Virus and CD4 is detected and quantified using an immunoassay such as an ELISA, or by performing quantitative PCR. Cell sorting techniques such as FACS are often used to isolate and quantify CD4$^+$ cells (as well as, e.g., CKR-5, fusin and other cell markers).

EXAMPLES

The following examples are provided by way of illustration only and not by way of limitation. Those of skill will readily recognize a variety of noncritical parameters which could be changed or modified to yield essentially similar results.

Example 1

Ribozymes Which Cleave CKR-5 and Ribozymes Which Cleave Fusin

Recently two co-receptors for HIV-1, CKR-5 and fusin have been identified. These cell surface proteins, along with CD4, mediate efficient viral infection. Whereas functional CD4 expression is required for immune competence, both receptors are not required for phenotypically normal immune responses. Accordingly, these mRNA encoding these receptors are targeted herein.

Ribozymes were designed to specifically cleave CKR-5 or fusin mRNA within cells, thereby reducing expression of CKR-5 and fusin on the cell surface, and inhibiting HIV infection of the cells.

Hairpin ribozymes were identified based on the presence of the required canonical sequence, BNGUC (SEQ ID NO: 3), in the target RNA. GUA targets are similarly found by examining the target RNA and finding the sequence GUA in the target RNA.

The coding sequence of CKR-5 contains 17 BNUGC (SEQ ID NO: 3) sites. Below are listed the cleavage site sequences, their respective distances from the translation initiation start site and the sequence of a corresponding hairpin ribozyme gene cleaves the site.

RZ cleavage sites within CKR-5 open reading frame and corresponding ribozyme genes.

1) 14 caagugucaaguccaa (SEQ ID NO: 4) TTGGACTTagaaCTTGaccagagaaacacacgttgtggtatattacctggta (SEQ ID NO: 5)
2) 150 ugcuggucauccucau (SEQ ID NO: 6) ATGAGGATagaaAGCAaccagagaaacacacgttgtggtatattacctggta (SEQ ID NO: 7)
3) 246 uuacugucccuucug (SEQ ID NO: 8) CAGAAGGGagaaGTAAaccagagaaacacacgttgtggtatattacctggta (SEQ ID NO: 9)
4) 301 aauguguucaacucuug (SEQ ID NO: 10) CAAGAGTTagaaCATTaccagagaaacacacgttgtggtatattacctggta (SEQ ID NO: 11)
5) 387 uggcugucguccaugc (SEQ ID NO: 12) GCATGGACagaaGCCAaccagagaaacacacgttgtggtatattacctggta (SEQ ID NO: 13)
6) 392 cugucguccaugcugu (SEQ ID NO: 14) ACAGCATGagaaACAGaccagagaaacacacgttgtggtatattacctggta (SEQ ID NO: 15)
7) 423 ggacggucaccuuugg (SEQ ID NO: 16) CCAAAGGTagaaGTCCaccagagaaacacacgttgtggtatattacctggta (SEQ ID NO: 17)
8) 476 uuugcgucucucccag (SEQ ID NO: 18) CTGGGAGAagaaCAAAaccagagaaacacacgttgtggtatattacctggta (SEQ ID NO: 19)
9) 553 auacagucaguaucaa (SEQ ID NO: 20) TTGATACTagaaGTATaccagagaaacacacgttgtggtatattacctggta (SEQ ID NO: 21)
10) 594 agauagucaucuuggg (SEQ ID NO: 22) CCCAAGATagaaATCTaccagagaaacacacgttgtggtatattacctggta (SEQ ID NO: 23)
11) 609 ggcugguccugccgcu (SEQ ID NO: 24) AGCGGCAGagaaAGCCaccagagaaacacacgttgtggtatattacctggta (SEQ ID NO: 25)
12) 624 ugcuugucauggucau (SEQ ID NO: 26) ATGACCATagaaAGCAaccagagaaacacacgttgtggtatattacctggta (SEQ ID NO: 27)
13) 630 ucauggucaucugcua (SEQ ID NO: 28) TAGCAGATagaaATGAaccagagaaacacacgttgtggtatattacctggta (SEQ ID NO: 29)
14) 670 ucggugucgaaaugag (SEQ ID NO: 30) CTCATTTCagaaCCGAaccagagaaacacacgttgtggtatattacctggta (SEQ ID NO: 31)
15) 759 acauuguccuucuccu (SEQ ID NO: 32) AGGAGAAGagaaATGTaccagagaaacacacgttgtggtatattacctggta (SEQ ID NO: 33)
16) 897 ccuuugucggggagaa (SEQ ID NO: 34) TTCTCCCCagaaAAGGaccagagaaacacacgttgtggtatattacctggta (SEQ ID NO: 35)
17) 927 ucuuagucuucuucca (SEQ ID NO: 36) TGGAAGAAagaaAAGAaccagagaaacacacgttgtggtatattacctggta (SEQ ID NO: 37)

RZ cleavage sites within fusin open reading frame and corresponding ribozyme genes are listed as follows:

1) 175 gauuggucauccuggu (SEQ ID NO: 38) ACCAGGATagaaAATCaccagagaaacacacgttgtggtatattacctggta (SEQ ID NO: 39)
2) 184 uccuggucauggguua (SEQ ID NO: 40) TAACCCATagaaAGGTaccagagaaacacacgttgtggtatattacctggta (SEQ ID NO: 41)
3) 240 caccugucauggccg (SEQ ID NO: 42) CGGCCACTagaaGGTGaccagagaaacacacgttgtggtatattacctggta (SEQ ID NO: 43)
4) 262 ucuuugucaucacgcu (SEQ ID NO: 44) AGCGTGATagaaAAGAaccagagaaacacacgttgtggtatattacctggta (SEQ ID NO: 45)
5) 334 aggcaguccaugucau (SEQ ID NO: 46) ATGACATGagaaGCCTaccagagaaacacacgttgtggtatattacctggta (SEQ ID NO: 47)
6) 352 acacagucaaccucua (SEQ ID NO: 48) TAGAGGTTagaaGTGTaccagagaaacacacgttgtggtatattacctggta (SEQ ID NO: 49)
7) 370 gcagugucccucauccu (SEQ ID NO: 50) AGGATGAGagaaCTGCaccagagaaacacacgttgtggtatattacctggta (SEQ ID NO: 51)
8) 392 caucagucuggaccgc (SEQ ID NO: 52) GCGGTCCAagaaGATGaccagagaaacacacgttgtggtatattacctggta (SEQ ID NO: 53)
9) 415 ccaucguccacgccac (SEQ ID NO: 54) GTGGCGTGagaaATGGaccagagaaacacacgttgtggtatattacctggta (SEQ ID NO: 55)
10) 431 caacagucagaggcca (SEQ ID NO: 56) TGGCCTCTagaaGTTGaccagagaaacacacgttgtggtatattacctggta (SEQ ID NO: 57)
11) 456 agguggucuauguugg (SEQ ID NO: 58) CCAACATAagaaACCTaccagagaaacacacgttgtggtatattacctggta (SEQ ID NO: 59)
12) 478 uuggcgucuggauccc (SEQ ID NO: 60) GGGATCCAagaaCCAAaccagagaaacacacgttgtggtatattacctggta (SEQ ID NO: 61)
13) 640 guauugucauccuguc (SEQ ID NO: 62) GACAGGATagaaATACaccagagaaacacacgttgtggtatattacctggta (SEQ ID NO: 63)
14) 648 auccuguccugcuauu (SEQ ID NO: 64) AATAGCAGagaaGGATaccagagaaacacacgttgtggtatattacctggta (SEQ ID NO: 65)
15) 678 aagcugucacacucca (SEQ ID NO: 66) TGGAGTGTagaaCGTTaccagagaaacacacgttgtggtatattacctggta (SEQ ID NO: 67)
16) 724 ccacagucauccucau (SEQ ID NO: 68) ATGAGGATagaaGTGGaccagagaaacacacgttgtggtatattacctggta (SEQ ID NO: 69)
17) 887 cuguugucugaaccc (SEQ ID NO: 70) GGGGTTCAagaaACAGaccagagaaacacacgttgtggtatattacctggta (SEQ ID NO: 71)
18) 969 agaggguccagccuca (SEQ ID NO: 72) TGAGGCTGagaaCTCTaccagagaaacacacgttgtggtatattacctggta (SEQ ID NO: 73)
19) 1029 acugagucugagucuu (SEQ ID NO: 74) AAGACTCAagaaCAGTaccagagaaacacacgttgtggtatattacctggta (SEQ ID NO: 75)
20) 1035 ucugagucuucaaguu (SEQ ID NO: 76) AACTTGAAagaaCAGAaccagagaaacacacgttgtggtatattacctggta (SEQ ID NO: 77)

The relative activities of these ribozymes are assessed by in vitro cleavage reactions using in vitro transcribed ribozymes and cognate substrates. Activities in vivo are established by HIV challenge of ribozyme expressing CD4/CKR-5 or CD4/fusin target cells.

Introduction of the anti-receptor ribozyme gene into the relevant cells is accomplished by various means including, but not limited to, viral transduction such as by Moloney-based retroviral vectors or by recombinant adeno-associated viral vectors. In addition, since the ribozymes do not target HIV RNAs directly, HIV-1 derived vectors are also used. Introduction of the gene is performed ex vivo and/or in vivo.

Example 2

In vitro studies of anti-CCR5 ribozyme on mRNA cleavage and anti-viral infection Screening 9 Rzs for in vitro activity.

As described in Example 1, a series of hairpin ribozymes are designed to cleave the mRNA for the chemokine receptor CCR5. There are 18 hairpin ribozyme target sites present in the protein coding region of the CCR5 mRNA corresponding to the consensus target site BNGUC (SEQ ID NO: 3). These initial 18 sites are reduced to a set of 9 favored ribozymes based on the criteria that helix 2 of the bound ribozyme-target complex contain at least two GC base pairs. The ribozymes are designated R5 and the numbering corresponds to the base position of the G in the GUC relative to the start site for translation initiation. The ribozymes are as follows: R5-14, R5-150, R5-387, R5-392, R5-423, R5-609, R5-624, R5-670, and R5-897.

The catalytic activity of each of the ribozymes is assessed by following a time course for the cleavage reaction. Cleavage reactions are performed at a substrate to ribozyme ratio of 13.5:1. The reactions are incubated at 30° C. for 2 hr with time points being taken at 0, 30, 60, 90, and 120 min. The products of the reaction are resolved by urea PAGE and the extent of cleavage quantitated on a Molecular Dynamics phosphorimager. The ribozymes which show the greatest level of activity during the time course are further analyzed by determining the catalytic efficiency for these ribozymes. The catalytic efficiency is defined as kcat/Km. Those ribozymes that approach 15% or more cleavage of the substrate after two hours and have catalytic efficiencies of two hundred or above are cloned into AAV Neo and AAV-NGFR vectors for testing in tissue culture.

Time Course Clevage of CCR5 Substrate RNAs by CCR5 Ribozymes

The cleavage capabilities of the nine preferred CCR5 ribozymes was assayed by following a time course for the clevage reaction. The concentration of ribozyme was 0.0052 $\mu$M and the substrate concentration was 0.072$\mu$M. The reactions were assembled on ice in buffer containing 4OmM Tris pH 7.5, 10 mM MgC12, 2mM spermidine and a final volume of 25$\mu$l. Five microliters of the each reaction was removed immediately for the 0 min time point and mixed with 5$\mu$l of termination mix (1 OM urea, 0.25% xylene cyanol, 0.25% bromophenol blue) and stored at –85° C. The remainders of each of the reactions were incubated at 37° C. for 2 hr with time points being taken at 30, 60, 90, and 120 min. Five microliters of each reaction was removed for each time point and mixed as described above. The products were resolved on a 20% polyacrylamide, 7M urea gel. Bands were visualized and quatitation was performed on a Molecular Dynamics phosphorimager. The results are summarized in FIG. 1.

Kinetic Parameters for CC-CKR5 Ribozymes

The kinetic constants kcat and Km were determined for each ribozyme that showed 20% or greater cleavage after 2 hour in the time course studies. Multiple turnover kinetic experiments were run in duplicate in a final volume of 10 $\mu$l. The concentration of ribozyme was either 2 or 4 nM and the substrate concentration was varied over a range from 2–200 nM. The reactions were assembled on ice in buffer containing 4 OmM Tris pH 7.5, 1 OmM MgCl$_2$ 2 mM spermidine. The reactions were immediately switched to 37° C. and incubated for the time necesary to accumulate enough products for quantitation. Reactions were terminated by the addition of 10 $\mu$l of termination mix (10 M urea, 0.25% xylene cyanol, 0.25% bromophenol blue). The reactions were heated at 65° C. for 2 min and products were resolved on a 20% polyacrylamide, 7M urea gel. Bands were visualized and quantitation was performed on a Molecular Dynamics phosphorimager. The data were plotted on a V versus V/S plot. The slope of this line gives the Km and the Y intercept divided by the concentration of ribozyme equals the kcat.

| Kinetic Parameters for CC-CKR5 Ribozymes | | | | |
|---|---|---|---|---|
| Ribozyme | n | Km(nM) | kcat | kcat/Km $10^4 M^{-1} min^{-1}$ |
| R5-14 | 2.00 | 8.90 | 0.065/min | 730.00 |
| R5-150 | 2.00 | 15.00 | 0.16/min | 1067.00 |
| R5-392 | 2.00 | 9.70 | 0.15/min | 1598.00 |
| R5-670 | 2.00 | 17.00 | 0.115/min | 676.00 |
| R5-897 | 2.00 | 65.00 | 0.12/min | 184.00 |

Cloning of Rz genes into AAV vectors.

The ribozymes that are derived from the above in vitro kinetic experiments are cloned into the vector AMFT. This vector contains the tRNA val promoter and either neo or NGFR as the selectable marker. This vector is modified to remove an extra BamHI site that is present in the polyA tail region of the neo gene. This facilitates cloning into the BamHI and Mlul sites downstream from the mRNAval promoter. These vectors are used to test the efficacy of individual ribozymes in both transient transfection assays and stable cell lines. Ribozymes with activity against the CCRS mRNA in tissue culture cells are further optimized by changing the length of helix 1 or by the addition of a tetraloop to helix 4 and loop 3.

Variants of these ribozymes that have the AAA at bases 22–24 of the ribozyme mutated to CGU are also generated. These ribozymes are disabled and do not cleave substrate, however, they still bind the substrate. Thus, these disabled ribozymes are used to determine whether the activity of the catalytic ribozymes in the cells is due catalysis or simple anti-sense properties of the bound ribozyme and/or what percentage of each property contributes to the activity observed in the cells.

In vitro studies of anti-CCR5 ribozyme on mRNA cleavage and anti-viral infection Target cells—In vivo studies of anti-CCR5 ribozymes resolve two questions:

(1) if ribozymes against CCR5 expressed in vivo can specifically and efficiently cleave CCR5 mRNA, and (2) if cleavage of intracellular CCR5 mRNA can protect cells from HIV-1 infection. PM1 T-cells, which express CCR5 and CXCR4 (fusin) are susceptible to both M-tropic and T-tropic HIV-1 variants, is a suitable immortalized cell line for use in the in vivo studies. Ideal anti-CCR5 ribozymes cleave CCR5 mRNA in PM1 cells render them resistant to M-tropic HIV-1 variants. In parallel experiments, CD34 derived macrophages are used to examine RZ-mediated protection in primary cells.

T-cells

Once ribozymes are selected, PM1 cells are infected with AAV-recombinants encoding the in vitro tested ribozymes. The infected cells are subjected to neomycin or NGFR selection. The stably transformed cells are examined for CCR5 mRNA expression and for the resistance to HIV-1 infection. The amount of intact CCR5 mRNA in the transformed PM1 cells is quantitated by Northern blotting. Resistance of these cells to HIV-1 infection is determined by two methods: (1) assay for HIV-1 env/CD4 mediated cell-cell fusion, and (2) an assay for HIV-1 infection. Cell-cell fusion assays are also carried out using the vaccinia expression system as follows. PM1 cells are infected by a vaccinia recombinant containing the reporter lacZ gene linked to a T7 promoter. Meanwhile, HeLa cells are co-infected by the vaccinia recombinant containing the T7 RNA polymerase gene linked to a vaccinia promoter and the vaccinia recombinant encoding HIV-1 env derived from Bal. Normal PM1 cells fuse with HeLa cells expressing env. As a result of fusion, b-galactosidase is synthesized and can be detected by a colorimetric assay.

Ribozymes against CCR5 which are stably expressed in the transformed PM1 cells and able to cleave CCR5 mRNA efficiently to reduce the expression of CCR5 on the cell surface inhibits cell-cell fusion. To ensure that the ribozyme is specific for CCR5, the fusion between the ribozyme-expressing PM1 cells and the HeLa cells expressing env derived from IHB (T-tropic) is examined. Ribozymes against CCR5 do not effect IHB env dependent fusion.

After the effectiveness of the ribozymes are confirmed by cell—cell fusion, they are further examined for their ability to render PM1 cells resistant to infection by M-tropic HIV isolates. The viral infection experiments are carried out as follows. PM1 cells are infected by T-tropic and M-tropic isolates. The viral protein p24 is quantitated by ELISA and used as an indicator for productive viral infection. The transformed PM1 cells which are negative for CCR5-dependent membrane fusion are resistant to infection by M-tropic (Bal, JRFL) but not T-tropic (LAV, IHB, RF) isolates. Once PM1 cells are transduced with AAV recombinant vectors encoding anti-CCR5 ribozymes to protect the cells from the infection by M-tropic HIV-1 isolates, inhibition of CCR5 expression in primary T lymphocytes and progenitor cells is verified.

Stem Cells/Macrophage studies $CD34^+$ cells are isolated from cord-blood by antibody selection. These cells are transduced with NGFR vectors and sorted by FACS. Selected cultures are maintained in the presence of IL-3, IL-6, SCF and GM-CSF for approximately 3 weeks and challenged with clinical HIV isolates, HIB and BAL-1. Supernatants are examined for p24 production and cells tested for RZ and CCR-5 expression.

Toxicity studies

Primary lymphocytes are activated and transduced with control vectors (no RZ) as well as RZ expressing vectors and selected by NGFR expression. These cells are expanded for several weeks and examined for differences in doubling time and dependence on IL-2. The ribozymes are then evaluated in Human clinical trials.

SEQUENCE LISTING

NNNBN*GUCNNNNNNNN (SEQ ID NO: 1)

NNNNN*GUANNNNNNNN (SEQ ID NO: 2)

BNUGC (SEQ ID NO: 3)

caagugucaaguccaa (SEQ ID NO: 4) TTGGACTTagaaCTTGaccagagaaacacacgttgtggtatattacctggta (SEQ ID NO: 5)

150 ugcuggucauccucau (SEQ ID NO: 6) ATGAGGATagaaAGCAaccagagaaacacacgttgtggtatattacctggta (SEQ ID NO: 7)

246 uuacuguccccuucug (SEQ ID NO: 8) CAGAAGGGagaaGTAAaccagagaaacacacgttgtggtatattacctggta (SEQ ID NO: 9)

301 aaugugucaacucuug (SEQ ID NO: 10) CAAGAGTTagaaCATTaccagagaaacacacgttgtggtatattacctggta (SEQ ID NO: 11)

387 uggcugucguccaugc (SEQ ID NO: 12) GCATGGACagaaGCCAaccagagaaacacacgttgtggtatattacctggta (SEQ ID NO: 13)

392 cugucguccaugcugu (SEQ ID NO: 14) ACAGCATGagaaACAGaccagagaaacacacgttgtggtatattacctggta (SEQ ID NO: 15)

423 ggacggucaccuuugg (SEQ ID NO: 16) CCAAAGGTagaaGTCCaccagagaaacacacgttgtggtatattacctggta (SEQ ID NO: 17)

476 uuugcgucucucccag (SEQ ID NO: 18) CTGGGAGAagaaCAAAaccagagaaacacacgttgtggtatattacctggta (SEQ ID NO: 19)

553 auacagucaguaucaa (SEQ ID NO: 20) TTGATACTagaaGTATaccagagaaacacacgttgtggtatattacctggta (SEQ ID NO: 21)

594 agauagucaucuuggg (SEQ ID NO: 22) CCCAAGATagaaATCTaccagagaaacacacgttgtggtatattacctggta (SEQ ID NO: 23)

609 ggcugguccugccgcu (SEQ ID NO: 24) AGCGGCAGagaaAGCCaccagagaaacacacgttgtggtatattacctggta (SEQ ID NO: 25)

624 ugcuugucauggucau (SEQ ID NO: 26) ATGACCATagaaAGCAaccagagaaacacacgttgtggtatattacctggta (SEQ ID NO: 27)

630 ucauggucaucugcua (SEQ ID NO: 28) TAGCAGATagaaATGAaccagagaaacacacgttgtggtatattacctggta (SEQ ID NO: 29)

670 ucggugucgaaaugag (SEQ ID NO: 30) CTCATTTCagaaCCGAaccagagaaacacacgttgtggtatattacctggta (SEQ ID NO: 31) 759 acauuguccuucuccu (SEQ ID NO: 32) AGGAGAAGagaaATGTaccagagaaacacacgttgtggtatattacctggta (SEQ ID NO: 33)

897 ccuuugucggggagaa (SEQ ID NO: 34) TTCTCCCCagaaAAGGaccagagaaacacacgttgtggtatattacctggta (SEQ ID NO: 35)

927 ucuuagucuucuucca (SEQ ID NO: 36) TGGAAGAAagaaAAGAaccagagaaacacacgttgtggtatattacctggta (SEQ ID NO: 37)

RZ cleavage sites within fusin open reading frame and corresponding ribozyme genes are listed as follows:

175 gauuggucauccuggu (SEQ ID NO: 38) ACCAGGATagaaAATCaccagagaaacacacgttgtggtatattacctggta (SEQ ID NO: 39) 184 uccuggucaugggiuua (SEQ ID NO: 40) TAACCCATagaaAGGTaccagagaaacacacgttgtggtatattacctggta (SEQ ID NO: 41)

240 caccugucaguggccg (SEQ ID NO: 42) CGGCCACTagaaGGTGaccagagaaacacacgttgtggtatattacctggta (SEQ ID NO: 43)

262 ucuuugucaucacgcu (SEQ ID NO: 44) AGCGTGATagaaAAGAaccagagaaacacacgttgtggtatattacctggta (SEQ ID NO: 45)

334 aggcaguccaugucau (SEQ ID NO: 46) ATGACATGagaaGCCTaccagagaaacacacgttgtggtatattacctggta (SEQ ID NO: 47)

352 acacagucaaccucua (SEQ ID NO: 48) TAGAGGTTagaaGTGTaccagagaaacacacgttgtggtatattacctggta (SEQ ID NO: 49)

370 gcaguguccucauccu (SEQ ID NO: 50) AGGATGAGagaaCTGCaccagagaaacacacgttgtggtatattacctggta (SEQ ID NO: 51)

392 caucagucuggaccgc (SEQ ID NO: 52) GCGGTCCAagaaGATGaccagagaaacacacgttgtggtatattacctggta (SEQ ID NO: 53)

415 ccaucguccacgccac (SEQ ID NO: 54) GTGGCGTGagaaATGGaccagagaaacacacgttgtggtatattacctggta (SEQ ID NO: 55)

431 caacagucagaggcca (SEQ ID NO: 56) TGGCCTCTagaaGTTGaccagagaaacacacgttgtggtatattacctggta (SEQ ID NO: 57)

456 agguggucuauguugg (SEQ ID NO: 58) CCAACATAa-
gaaACCTaccagagaaacacacgttgtggtatattacctggta (SEQ ID NO: 59)

478 uuggcgucuggauccc (SEQ ID NO: 60) GGGATCCAa-
gaaCCAAaccagagaaacacacgttgtggtatattacctggta (SEQ ID NO: 61)

640 guauugucauccuguc (SEQ ID NO: 62) GACAGGATa-
gaaATACaccagagaaacacacgttgtggtatattacctggta (SEQ ID NO: 63)

648 auccuguccugcuauu (SEQ ID NO: 64) AATAGCA-
GagaaGGATaccagagaaacacacgttgtggtatattacctggta (SEQ ID NO: 65)

678 aagcugucacacucca (SEQ ID NO: 66) TGGAGTGTa-
gaaCGTTaccagagaaacacacgttgtggtatattacctggta (SEQ ID NO: 67)

724 ccacagucauccucau (SEQ ID NO: 68) ATGAGGATa-
gaaGTGGaccagagaaacacacgttgtggtatattacctggta (SEQ ID NO: 69)

887 cuguugucugaacccc (SEQ ID NO: 70) GGGGTTCAa-
gaaACAGaccagagaaacacacgttgtggtatattacctggta (SEQ ID NO: 71)

969 agaggguccagccuca (SEQ ID NO: 72) TGAGGCT-
GagaaCTCTaccagagaaacacacgttgtggtatattacctggta (SEQ ID NO: 73)

1029 acugagucugagucuu (SEQ ID NO: 74) AAGACTCAa-
gaaCAGTaccagagaaacacacgttgtggtatattacctggta (SEQ ID NO: 75)

1035 ucugagucuucaaguu (SEQ ID NO: 76) AACTTGAAa-
gaaCAGAaccagagaaacacacgttgtggtatattacctggta (SEQ ID NO: 77)

---

What is claimed is:

1. An endoribonuclease nucleic acid encoding a ribozyme, wherein the ribozyme cleaves in vitro an RNA comprising a target subsequence selected from the group of target subsequences consisting of SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, and conservative modifications thereof.

2. The endoribonuclease nucleic acid of claim 1, wherein the endoribonuclease nucleic acid comprises a nucleic acid subsequence complementary to the selected target subsequence.

3. The endoribonuclease nucleic acid of claim 1, wherein the endonuclease nucleic acid encodes a ribozyme selected from the group of ribozymes consisting of SEQ ID NOs.: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, and conservative modifications thereof.

4. The endo-ribonuclease nucleic acid of claim 1, wherein the ribozyme cleaves a target nucleic acid 5' of a GUC site.

5. The endo-ribonuclease nucleic acid of claim 1, wherein the nucleic acid is operably linked to a promoter.

6. The endo-ribonuclease nucleic acid of claim 5, wherein the promoter is a $CD4^+$ cell-specific promoter.

7. The endo-ribonuclease nucleic acid of claim 1, wherein the nucleic acid is encoded by an expression vector.

8. The endo-ribonuclease nucleic acid of claim 1, wherein the nucleic acid is encoded by an expression vector, wherein the expression vector is an AAV vector.

9. The endo-ribonuclease nucleic acid of claim 5, wherein the promoter is a pol III promoter.

10. The endo-ribonuclease nucleic acid of claim 1, wherein the nucleic acid encodes a ribozyme modified from the group of ribozymes consisting of SEQ ID NOs.: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, and 77, wherein the modification consists of an modification selected from the group of modifications consisting of a loop 3 nucleotide substitution, a helix 4 nucleotide substitution, lengthening the helix 4 domain, shortening the helix 4 domain, lengthening the helix 3 domain, shortening the helix 3 domain, shortening the helix 1 domain, lengthening the helix 1 domain, adding DNA bases to the ribozyme, and conversion of the ribozyme to an RNA phosphothio analog.

11. The endo-ribonuclease nucleic acid of claim 1, wherein the endo-ribonuclease nucleic acid encodes a modified ribozyme derived from a ribozyme selected from the group of ribozymes consisting of SEQ ID NOs.: 5, 7, 9, 11, 13, 15, 17, 19, 21, 23, 25, 27, 29, 31, 3, 35, 37, 39, 41, 43, 45, 47, 49, 51, 53, 55, 57, 59, 61, 63, 65, 67, 69, 71, 73, 75, and 77.

12. The endo-ribonuclease nucleic acid of claim 11, wherein the modified ribozyme is derived from the group of ribozymes by increasing the number of complementary nucleotides in helix 1.

13. The endo-ribonuclease nucleic acid of claim 11, wherein the modified ribozyme is derived from the group of ribozymes by decreasing the number of complementary nucleotides in helix 1.

* * * * *

```
            SEQUENCE LISTING (1) GENERAL INFORMATION:

(iii) NUMBER OF SEQUENCES: 77

(2) INFORMATION FOR SEQ ID NO:1:

(i) SEQUENCE CHARACTERISTICS:
         (A) LENGTH: 16 base
pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ
ID NO:1:

NNNBNGUCNN NNNNNN

16

(2) INFORMATION FOR SEQ ID NO:2:

(i) SEQUENCE CHARACTERISTICS:
         (A) LENGTH: 16 base
pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ
ID NO:2:

NNNNNGUANN NNNNNN

16

(2) INFORMATION FOR SEQ ID NO:3:

(i) SEQUENCE CHARACTERISTICS:
         (A) LENGTH: 5 base p
airs
         (B) TYPE: nucleic acid
         (C) STRANDEDNESS: single
         (D) TOPOLOGY: linear (ii) MOLECULE TYPE: RNA
```

(xi) SEQUENCE DESCRIPTION: SEQ ID NO:3:

BNUGC

5

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:4:

CAAGUGUCAA GUCCAA

16

(2) INFORMATION FOR SEQ ID NO:5:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TTGGACTTAG AACTTGACCA GAGAAACACA CGTTGTGGTA TATTACCTGG TA

52

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:6:

UGCUGGUCAU CCUCAU

16

(2) INFORMATION FOR SEQ ID NO:7:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ATGAGGATAG AAAGCAACCA GAGAAACACA CGTTGTGGTA TATTACCTGG TA
          52

(2) INFORMATION FOR SEQ ID NO:8:

(i) SEQUENCE CHARACTERISTICS:
        (A) LENGTH: 16 base
pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ
ID NO:8:

UUACUGUCCC CUUCUG

16

(2) INFORMATION FOR SEQ ID NO:9:

(i) SEQUENCE CHARACTERISTICS:
        (A) LENGTH: 52 base
pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ
ID NO:9:

CAGAAGGGAG AAGTAAACCA GAGAAACACA CGTTGTGGTA TATTACCTGG TA
          52

(2) INFORMATION FOR SEQ ID NO:10:

(i) SEQUENCE CHARACTERISTICS:
        (A) LENGTH: 16 base
pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ
ID NO:10:

AAUGUGUCAA CUCUUG

16

(2) INFORMATION FOR SEQ ID NO:11:

(i) SEQUENCE CHARACTERISTICS:
        (A) LENGTH: 52 base
pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ
ID NO:11:

CAAGAGTTAG AACATTACCA GAGAAACACA CGTTGTGGTA TATTACCTGG TA
          52

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:12:

UUGCUGUCGU CCAUGC 16

(2) INFORMATION FOR SEQ ID NO:13:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GCATGGACAG AAGCCAACCA GAGAAACACA CGTTGTGGTA TATTACCTGG TA 52

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:14:

CUGUCGUCCA UGCUGU 16

(2) INFORMATION FOR SEQ ID NO:15:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

ACAGCATGAG AAACAGACCA GAGAAACACA CGTTGTGGTA TATTACCTGG TA 52

(2) INFORMATION FOR SEQ ID NO:16:

(i) SEQUENCE CHARACTERISTICS:

(A) LENGTH: 16 base
pairs
                (B) TYPE: nucleic acid
                (C) STRANDEDNESS: single
                (D) TOPOLOGY: linear (ii) MOLECULE TYPE: RNA (xi) SEQUENCE DESCRIPTION: SEQ
ID NO:16:

GGACGGUCAC CUUUGG

16

(2) INFORMATION FOR SEQ ID NO:17:

(i) SEQUENCE CHARACTERISTICS:
            (A) LENGTH: 52 base
pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ
ID NO:17:

CCAAAGGTAG AAGTCCACCA GAGAAACACA CGTTGTGGTA TATTACCTGG TA
            52

(2) INFORMATION FOR SEQ ID NO:18:

(i) SEQUENCE CHARACTERISTICS:
            (A) LENGTH: 16 base
pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ
ID NO:18:

UUUGCGUCUC UCCCAG

16

(2) INFORMATION FOR SEQ ID NO:19:

(i) SEQUENCE CHARACTERISTICS:
            (A) LENGTH: 52 base
pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ
ID NO:19:

CTGGGAGAAG AACAAAACCA GAGAAACACA CGTTGTGGTA TATTACCTGG TA
            52

(2) INFORMATION FOR SEQ ID NO:20:

(i) SEQUENCE CHARACTERISTICS:
            (A) LENGTH: 16 base
pairs
            (B) TYPE: nucleic acid
            (C) STRANDEDNESS: single (D) TOPOLOGY: linear (ii) MOLECULE TYPE: RNA (xi) SEQUENCE DESCRIPTION: SEQ ID NO:20:

AUACAGUCAG UAUCAA 16

(2) INFORMATION FOR SEQ ID NO:21:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:21:

TTGATACTAG AAGTATACCA GAGAAACACA CGTTGTGGTA TATTACCTGG TA 52

(2) INFORMATION FOR SEQ ID NO:22:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: RNA (xi) SEQUENCE DESCRIPTION: SEQ ID NO:22:

AGAUAGUCAU CUUGGG 16

(2) INFORMATION FOR SEQ ID NO:23:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:23:

CCCAAGATAG AAATCTACCA GAGAAACACA CGTTGTGGTA TATTACCTGG TA 52

(2) INFORMATION FOR SEQ ID NO:24:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: RNA (xi) SEQUENCE DESCRIPTION: SEQ ID NO:24:

GGCUGGUCCU GCCGCU

16

(2) INFORMATION FOR SEQ ID NO:25:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

AGCGGCAGAG AAAGCCACCA GAGAAACACA CGTTGTGGTA TATTACCTGG TA

52

(2) INFORMATION FOR SEQ ID NO:26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:26:

UGCUUGUCAU GGUCAU

16

(2) INFORMATION FOR SEQ ID NO:27:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

ATGACCATAG AAAGCAACCA GAGAAACACA CGTTGTGGTA TATTACCTGG TA

52

(2) INFORMATION FOR SEQ ID NO:28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:28:

UCAUGGUCAU CUGCUA

16

(2) INFORMATION FOR SEQ ID NO:29:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TAGCAGATAG AAATGAACCA GAGAAACACA CGTTGTGGTA TATTACCTGG TA    52

(2) INFORMATION FOR SEQ ID NO:30:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:30:

UCGGUGUCGA AAUGAG

16

(2) INFORMATION FOR SEQ ID NO:31:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

CTCATTTCAG AACCGAACCA GAGAAACACA CGTTGTGGTA TATTACCTGG TA    52

(2) INFORMATION FOR SEQ ID NO:32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:32:

ACAUUGUCCU UCUCCU

16

(2) INFORMATION FOR SEQ ID NO:33:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

AGGAGAAGAG AAATGTACCA GAGAAACACA CGTTGTGGTA TATTACCTGG TA      52

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:34:

CCUUUGUCGG GGAGAA      16

(2) INFORMATION FOR SEQ ID NO:35:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

TTCTCCCCAG AAAAGGACCA GAGAAACACA CGTTGTGGTA TATTACCTGG TA      52

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:36:

UCUUAGUCUU CUUCCA      16

(2) INFORMATION FOR SEQ ID NO:37:

(i) SEQUENCE CHARACTERISTICS:

(A) LENGTH: 52 base
pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ
ID NO:37:

TGGAAGAAAG AAAAGAACCA GAGAAACACA CGTTGTGGTA TATTACCTGG TA
            52

(2) INFORMATION FOR SEQ ID NO:38:

(i) SEQUENCE CHARACTERISTICS:
        (A) LENGTH: 16 base
pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ
ID NO:38:

GAUUGGUCAU CCUGGU

16

(2) INFORMATION FOR SEQ ID NO:39:

(i) SEQUENCE CHARACTERISTICS:
        (A) LENGTH: 52 base
pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ
ID NO:39:

ACCAGGATAG AAAATCACCA GAGAAACACA CGTTGTGGTA TATTACCTGG TA
            52

(2) INFORMATION FOR SEQ ID NO:40:

(i) SEQUENCE CHARACTERISTICS:
        (A) LENGTH: 16 base
pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ
ID NO:40:

UCCUGGUCAU GGGUUA

16

(2) INFORMATION FOR SEQ ID NO:41:

(i) SEQUENCE CHARACTERISTICS:
        (A) LENGTH: 52 base
pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ
ID NO:41:

TAACCCATAG AAAGGTACCA GAGAAACACA CGTTGTGGTA TATTACCTGG TA
          52

(2) INFORMATION FOR SEQ ID NO:42:

(i) SEQUENCE CHARACTERISTICS:
          (A) LENGTH: 16 base
pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ
ID NO:42:

CACCUGUCAG UGGCCG

16

(2) INFORMATION FOR SEQ ID NO:43:

(i) SEQUENCE CHARACTERISTICS:
          (A) LENGTH: 52 base
pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ
ID NO:43:

CGGCCACTAG AAGGTGACCA GAGAAACACA CGTTGTGGTA TATTACCTGG TA
          52

(2) INFORMATION FOR SEQ ID NO:44:

(i) SEQUENCE CHARACTERISTICS:
          (A) LENGTH: 16 base
pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ
ID NO:44:

UCUUUGUCAU CACGCU

16

(2) INFORMATION FOR SEQ ID NO:45:

(i) SEQUENCE CHARACTERISTICS:
          (A) LENGTH: 52 base
pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ
ID NO:45:

AGCGTGATAG AAAAGAACCA GAGAAACACA CGTTGTGGTA TATTACCTGG TA
            52

(2) INFORMATION FOR SEQ ID NO:46:

(i) SEQUENCE CHARACTERISTICS:
         (A) LENGTH: 16 base
pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ
ID NO:46:

AGGCAGUCCA UGUCAU

16

(2) INFORMATION FOR SEQ ID NO:47:

(i) SEQUENCE CHARACTERISTICS:
         (A) LENGTH: 52 base
pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ
ID NO:47:

ATGACATGAG AAGCCTACCA GAGAAACACA CGTTGTGGTA TATTACCTGG TA
            52

(2) INFORMATION FOR SEQ ID NO:48:

(i) SEQUENCE CHARACTERISTICS:
         (A) LENGTH: 16 base
pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ
ID NO:48:

ACACAGUCAA CCUCUA

16

(2) INFORMATION FOR SEQ ID NO:49:

(i) SEQUENCE CHARACTERISTICS:
         (A) LENGTH: 52 base
pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ
ID NO:49:

TAGAGGTTAG AAGTGTACCA GAGAAACACA CGTTGTGGTA TATTACCTGG TA (2) INFORMATION FOR SEQ ID NO:50:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:50:

GCAGUGUCCU CAUCCU 16

(2) INFORMATION FOR SEQ ID NO:51:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

AGGATGAGAG AACTGCACCA GAGAAACACA CGTTGTGGTA TATTACCTGG TA 52

(2) INFORMATION FOR SEQ ID NO:52:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:52:

CAUCAGUCUG GACCGC 16

(2) INFORMATION FOR SEQ ID NO:53:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

GCGGTCCAAG AAGATGACCA GAGAAACACA CGTTGTGGTA TATTACCTGG TA 52

(2) INFORMATION FOR SEQ ID NO:54:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO:54:

CCAUCGUCCA CGCCAC

16

(2) INFORMATION FOR SEQ ID NO:55:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

GTGGCGTGAG AAATGGACCA GAGAAACACA CGTTGTGGTA TATTACCTGG TA      52

(2) INFORMATION FOR SEQ ID NO:56:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:56:

CAACAGUCAG AGGCCA

16

(2) INFORMATION FOR SEQ ID NO:57:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

TGGCCTCTAG AAGTTGACCA GAGAAACACA CGTTGTGGTA TATTACCTGG TA      52

(2) INFORMATION FOR SEQ ID NO:58:

(i) SEQUENCE CHARACTERISTICS:
        (A) LENGTH: 16 base pairs (B) TYPE: nucleic acid
        (C) STRANDEDNESS: single
        (D) TOPOLOGY: linear (ii) MOLECULE TYPE: RNA (xi) SEQUENCE DESCRIPTION: SEQ
ID NO:58:

AGGUGGUCUA UGUUGG

16

(2) INFORMATION FOR SEQ ID NO:59:

(i) SEQUENCE CHARACTERISTICS:
        (A) LENGTH: 52 base
pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ
ID NO:59:

CCAACATAAG AAACCTACCA GAGAAACACA CGTTGTGGTA TATTACCTGG TA
            52

(2) INFORMATION FOR SEQ ID NO:60:

(i) SEQUENCE CHARACTERISTICS:
        (A) LENGTH: 16 base
pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ
ID NO:60:

UUGGCGUCUG GAUCCC

16

(2) INFORMATION FOR SEQ ID NO:61:

(i) SEQUENCE CHARACTERISTICS:
        (A) LENGTH: 52 base
pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ
ID NO:61:

GGGATCCAAG AACCAAACCA GAGAAACACA CGTTGTGGTA TATTACCTGG TA
            52

(2) INFORMATION FOR SEQ ID NO:62:

(i) SEQUENCE CHARACTERISTICS:
        (A) LENGTH: 16 base
pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:62:

GUAUUGUCAU CCUGUC                                                    16

(2) INFORMATION FOR SEQ ID NO:63:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:63:

GACAGGATAG AAATACACCA GAGAAACACA CGTTGTGGTA TATTACCTGG TA            52

(2) INFORMATION FOR SEQ ID NO:64:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:64:

AUCCUGUCCU GCUAUU                                                    16

(2) INFORMATION FOR SEQ ID NO:65:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

AATAGCAGAG AAGGATACCA GAGAAACACA CGTTGTGGTA TATTACCTGG TA            52

(2) INFORMATION FOR SEQ ID NO:66:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:66:

AAGCUGUCAC ACUCCA

16

(2) INFORMATION FOR SEQ ID NO:67:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

TGGAGTGTAG AACGTTACCA GAGAAACACA CGTTGTGGTA TATTACCTGG TA

52

(2) INFORMATION FOR SEQ ID NO:68:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:68:

CCACAGUCAU CCUCAU

16

(2) INFORMATION FOR SEQ ID NO:69:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

ATGAGGATAG AAGTGGACCA GAGAAACACA CGTTGTGGTA TATTACCTGG TA

52

(2) INFORMATION FOR SEQ ID NO:70:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:70:

CUGUUGUCUG AACCCC

16

(2) INFORMATION FOR SEQ ID NO:71:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:71:

GGGGTTCAAG AAACAGACCA GAGAAACACA CGTTGTGGTA TATTACCTGG TA 52

(2) INFORMATION FOR SEQ ID NO:72:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:72:

AGAGGGUCCA GCCUCA 16

(2) INFORMATION FOR SEQ ID NO:73:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:73:

TGAGGCTGAG AACTCTACCA GAGAAACACA CGTTGTGGTA TATTACCTGG TA 52

(2) INFORMATION FOR SEQ ID NO:74:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:74:

ACUGAGUCUG AGUCUU 16

(2) INFORMATION FOR SEQ ID NO:75:

(i) SEQUENCE CHARACTERISTICS:
            (A) LENGTH: 52 base
pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ
ID NO:75:

AAGACTCAAG AACAGTACCA GAGAAACACA CGTTGTGGTA TATTACCTGG TA
            52

(2) INFORMATION FOR SEQ ID NO:76:

(i) SEQUENCE CHARACTERISTICS:
            (A) LENGTH: 16 base
pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ
ID NO:76:

UCUGAGUCUU CAAGUU

16

(2) INFORMATION FOR SEQ ID NO:77:

(i) SEQUENCE CHARACTERISTICS:
            (A) LENGTH: 52 base
pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ
ID NO:77:

AACTTGAAAG AACAGAACCA GAGAAACACA CGTTGTGGTA TATTACCTGG TA
            52